United States Patent [19]

Kun et al.

[11] Patent Number: 6,004,978
[45] Date of Patent: Dec. 21, 1999

[54] METHODS OF TREATING CANCER WITH AROMATIC NITRO AND NITROSO COMPOUNDS AND THEIR METABOLITES

[75] Inventors: Ernest Kun, Mill Valley; Jerome Mendeleyev, San Francisco; Eva Kirsten, Daly City, all of Calif.

[73] Assignee: Octamer, Inc., Mill Valley, Calif.

[21] Appl. No.: 08/473,044

[22] Filed: Jun. 6, 1995

Related U.S. Application Data

[60] Division of application No. 08/076,313, Jun. 11, 1993, Pat. No. 5,464,871, which is a continuation-in-part of application No. 08/060,409, May 12, 1993, abandoned.

[51] Int. Cl.⁶ .......................... A61K 31/47; A61K 31/35; A61K 31/165
[52] U.S. Cl. .......................... 514/309; 514/457; 514/617; 514/619
[58] Field of Search .................. 514/617, 619, 514/309, 457

[56] References Cited

U.S. PATENT DOCUMENTS

| | | | |
|---|---|---|---|
| 2,006,735 | 7/1935 | Fischer | 564/166 |
| 2,669,583 | 2/1954 | Clinton | 564/166 |
| 2,937,204 | 5/1960 | Harris | 564/166 |
| 3,161,564 | 12/1964 | Morehouse | 564/166 |
| 3,228,833 | 1/1966 | Crounse | 564/166 |
| 5,283,352 | 2/1994 | Backstrom | 564/166 |

FOREIGN PATENT DOCUMENTS

| | | |
|---|---|---|
| 0 371 560 | 6/1987 | European Pat. Off. . |
| 0 366 061 | 5/1990 | European Pat. Off. . |
| WO-A-91 04663 | 4/1991 | WIPO . |
| WO-A-92 06687 | 4/1993 | WIPO . |

OTHER PUBLICATIONS

1930, *Chem. Abstracts* 24:3367.
1978, *Virus Diseases* Crown Publishers, NY, 1–6.
1982, *The Merck Manual,* 14th Ed. 170.
1987, *The Merck Manual,* 15th Ed. 1218–1225.
Aldovini et al., 1990, "Mutations of RNA and protein sequences involved in human immunodeficiency virus Type I packaging result in production of noninfectious virus," *J. Virol.* 64:1920–1926.
Buki et al., 1991, "Destabilization of $Zn^{2+}$ coordination in ADP–ribose transferase(polymerizing) by 6–nitroso–1, 2–benzopyrone coincidental with inactivation of the polymerase but not the DNA binding function," *FEBS Lett.* 290:181–185.
Donegan et al., eds., 1988, *Cancer of the Breast* p. 504.
Gorelick et al., 1988, "Point mutants and Moloney murine leukemia virus that fail to package viral RNA: Evidence for specific RNA recognition by a "zinc finger–like" protein sequence," *Proc. Natl. Acad. Sci. USA* 85:8420–8424.
Gorelick et al., 1990, "Noninfectious Human Immunodeficiency Virus Type 1 Mutants Deficient in Genomic RNA", *J. Virol.* 64:3207–3211.
Gradwohl et al., 1990, "The second zinc–finger domain of poly(ADP–ribose) polymerase determines specificity for single–stranded breaks in DNA," *Proc. Natl. Acad. Sci. USA* 87:2990–2994.
Hakam et al., 1987, "Catalytic Activities of Synthetic Octa-deoxyribonucleotides as Coenzymes of Poly(ADP–ribose) Polymerase and the Identification of a New Enzyme Inhibitory Site," *FEBS Lett.* 212:73–78.
Henderson et al., 1981, "Primary Structure of the Low Molecular Weight Nucleic Acid–binding Proteins of Murine Leukemia Viruses," *Biol. Chem.* 256:8400–8406.
Hickman, John A., 1975, "Protection Against the Effects of the Antitumour Agent CB 1954 by Certain Imidazoles and Related Compounds," *Biochemical Pharmacology* 24:1947–1952.
Hodgkiss et al., 1991, "Fluorescent Markers for Hypoxic Cells," *Biochemical Pharmacology* 41(4):533–541.
Kozakova et al., 1982, "Anion radicals of substituted nitrobenzonitriles and m–dinitrobenzonitriles," *Chem. Abstracts* 97:23081n.
Kozlova, 1986, *Chem. Abstracts* 104:5699k.
Lever et al., 1989, "Identification of a Sequence Required for Efficient Packaging of Human Immunodeficiency Virus Type 1 RNA into Virus", *J. Virol.* 63:4085–4087.
Meric and Goff, 1989, "Characterization of Moloney Murine Leukemia Virus Mutants with Single–Amino–Acid Substitutions in the Cys–His Box of the Nucleocapsid," *J. Virol.* 63:1558–1568.
Paruthi et al., 1976, *Chem. Abstracts* 85:20446h.
Ram and Ehrenkaufer, 1984, "A General Procedure to Mild and Rapid Reduction of Aliphatic and Aromatic Nitro Compounds Using Ammonium Formate as a Catalytic Hydrogen Transfer Agent," *Chem. Abstracts* 101:230049f.
Rice et al., 1992, "Induction of endonuclease–mediaed apoptosis in tumor cells by C–nitroso–substituted ligands of poly (ADP–ribose) polymerase," *Proc. Natl. Acad. Sci. USA* 89:7703–7707.
Sinha et al., 1985, *Chem. Abstracts* 103:71216f.

*Primary Examiner*—Jerome D. Goldberg
*Attorney, Agent, or Firm*—Albert P. Halluin; Howrey & Simon

[57] ABSTRACT

Unsubstituted or substituted halo nitro and nitroso compounds and their metabolites are potent, selective and nontoxic inhibitors and suppressants of cancer growth and viral infections in a mammalian host. The compounds are particularly useful for treatment and suppression of tumors and viruses associated with breast cancer, AIDS, herpetic episodes and cytomegaloviral infections. The methods of treatment of tumorigenic and viral diseases by halo nitro and nitroso compounds and their metabolites are described.

11 Claims, 4 Drawing Sheets

METHODS OF TREATING CANCER WITH AROMATIC NITRO AND NITROSO COMPOUNDS AND THEIR METABOLITES

This is a division, of application Ser. No. 08/076,313, filed Jun. 11, 1993; now U.S. Pat. No. 5,464,871 which is a CIP of application Ser. No. 08/060,409 filed May 12, 1993 now abandoned.

BACKGROUND OF THE INVENTION

Field of the Invention

The present invention relates generally to novel aromatic nitro and nitroso compounds and their metabolites useful as potent, selective, stable and safe anti-tumor and anti-viral agents, and to a method of treatment of tumorigenic and viral diseases using aromatic nitro and nitroso compounds and their metabolites. More specifically, it relates to the use of various nitro compounds including halo-nitro-estradiol, halo-nitroso-estradiol, halo-nitro-estrone, halo-nitroso-estrone, halo-nitro-estriol, halo-nitroso-estriol, halo-nitro-equilenin, halo-nitroso-equilenin, halo-nitro-equilin, halo-nitroso-equilin, halo-nitro-stilbestrol, halo-nitroso-stilbestrol, 4-halo-3-nitrobenzamide, 4-iodo-3-nitrobenzamide, 4-halo-3-nitrobenzopyrone, 4-iodo-3-nitrobenzopyrone, 5-halo-6-nitro-1,2-benzopyrones, 5-iodo-6-nitro-1,2-benzopyrones, 6-nitro-1,2-benzopyrone, 3-nitrobenzamide, 5-nitro-1(2H)-isoquinoline, 7-nitro-1(2H)-isoquinoline, 8-nitro-1(2H)-isoquinoline, 2-nitrobenzamide, and 4-nitrobenzamide their homologues and salts, in suppressing and inhibiting tumor growth and the growth of certain viruses in a mammalian host.

The State of Art and Related Disclosures

Cancer and viral infections are a serious threat to modern society. Malignant cancerous growths, due to their unique characteristics, pose serious challenges for modern medicine. These characteristics include: uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation.

A particularly difficult type of cancer to treat is breast cancer. Approximately 130,000 new cases of breast cancer occur per year in the United States and 70% of these patients will ultimately have recurrence and die of the disease. (*Cancer of the Breast,* Donegan, W. L., et al. eds., p.504 (1988)).

Antineoplastic chemotherapy currently encompasses several groups of drugs including alkylating agents, purine antagonists and antitumor antibiotices. Alkylating agents alkylate cell proteins and nucleic acids preventing cell replication, disrupting cellular metabolism and eventually leading to cell death. Typical alkylating agents are nitrogen mustard, cyclophosphamide and chlorambucil. Toxicities associated with alkylating agents treatment include nausea, vomiting, alopecia, hemorrhagic cystitis, pulmonary fibrosis and an increased risk of development of acute leukemia.

Purine, pyrimidine and folate antagonists are cell cycle and phase specific and, in order to promote an anti-tumor effect, they require cells to be in the cell replication cycle and in the DNA synthesis phase of replication. The purine antagonists such as 6-mercaptopurine or 6-thioguanidine inhibit de novo purine synthesis and interconversion of purines. The pyrimidine antagonists, such as cytarabine, 5-fluorouracil or floxuridine inhibit DNA synthesis by inhibiting deoxycytidylate kinase and DNA polymerase.

Folate antagonists, eg. methotrexates, bind tightly with the intracellular enzyme dihydrofolate reductase ultimately leading to cell death resulting from an inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and teniposide generally inhibit mitosis and DNA synthesis and RNA dependent protein synthesis. Toxicities of these drugs are similar to those described above and include myopathy, myelosuppression, peripheral neuropathy, vomiting, nausea and alopecia.

Antitumor antibiotics such as doxorubicin, daunorubicin and dactinomycin act as intercalators of DNA, preventing cell replication, inhibiting synthesis of DNA-dependent RNA and inhibiting DNA polymerase. Bleomycin causes scission of DNA and mitomycin acts as inhibitor of DNA synthesis by bifunctional alkylation. Toxicities of these antibiotics are numerous and severe and include necrosis, myelosuppression, anaphylactic reactions, anorexia, dose-dependent cardiotoxicity and pulmonary fibrosis.

Other compounds used for chemotherapeutical treatment of cancer are inorganic ions such as cisplatin, biologic response modifiers such as interferon, enzymes and hormones. All these compounds, similarly to those mentioned above, are accompanied by toxic adverse reactions.

Endocrine therapy in the treatment of breast cancer is an alternative to chemotherapy. Estrogen is a highly potent mammary mitogen and is the major stimulus for the growth of hormone-dependent breast cancer. Estradiol (an estrogen) is believed to stimulate breast growth (mitogenesis) by binding to nuclear estrogen receptors which stimulate increases in RNA polymerase activity and ultimately cancer cell growth. (*Cancer of the Breast,* Donegan, W. L., et al. eds., p.504 (1988)).

Thus, it would be extremely advantageous to provide safe and non-toxic chemotherapeutic compounds which would effectively inhibit cancer cell proliferation and suppress neoplastic growth. (*The Merck Manual,* 1218–1225 (1987), 15th Ed.). In particular, it would be advantageous to provide estrogen-like non-toxic chemotherapeutic molecules that would specifically target breast cancers. Novel compounds of this invention provide such treatment.

Similar to cancer, the high degree of infectiousness and fast reproduction cycle of viruses within host organisms make viruses a nuisance and a health hazard.

There is no simple treatment of viral diseases. Viruses are not susceptible to antibiotics. The only available treatment of viral diseases is chemotherapy utilizing viral replication inhibitors in host cells (*The Merck Manual,* 170 (1982), 14th Ed.). Examples of these chemical agents are idoxuridine, acyclovir, ribavirin, vidarabine, gancyclovir, adenine arabinoside (ABA-A) and AZT. These, and other viral replication inhibitors, however, are cytotoxic, hepatotoxic, neurotoxic, nephrotoxic and teratogenic (*Virus Diseases,* 1–6 (1978), Crown Publishers, New York).

Human immunodeficiency virus (HIV) infections known as acquired immunodeficiency syndrome (AIDS), presently constitute a worldwide health hazard. HIV infections are almost always fatal due to a weakened immunoresistance, leading to opportunistic infections, malignancies and neurologic lesions.

There is no effective treatment for AIDS other than the treatment of the opportunistic infections, neoplasms and other complications. Available cytostatic (AZT) and antiviral (acyclovir) drugs are extremely toxic and cause severe adverse reactions.

Thus it would be highly desirable to have available an effective and yet nontoxic treatment of viral diseases, in particular, AIDS.

Herpes simplex virus type-1 and 2 are also wide spread infections. They may occur in AIDS patients as one of the opportunistic infections. Type-1 HSV strain (HSV-1) commonly causes herpes labialism located on a lip, and keratitis, an inflammation of the cornea. Type-2 HSV is usually located on or around the genital area and is generally transmitted primarily by direct contact with herpetic sore or lesions. HSV-2 has been related to the development of uterine cancer.

Herpes simplex virus is very infectious and is rapidly and easily transferable by contact. There is no specific therapy to this extremely painful viral infection. Current treatment of HSV infections is limited primarily to systemic administration of the above-mentioned antiviral drugs with corresponding adverse side affects.

The antiviral agents used for HSV treatment are nonselective inhibitors of HSV replication affecting the replication of normal cells as well. Therefore, when used in doses large enough to inactivate all of the active herpes viruses dormant in the sensory ganglia, these compounds may also be highly disruptive to host cell DNA replication.

Thus, it would be advantageous to have available nontoxic treatment of HSV infections.

Cytomegalovirus (CMV), a dangerous co-infection of HIV, is a subgroup of highly infectious viruses having the propensity for remaining latent in man. CMVs are very common among the adult population and as many as 90% of adults have been exposed to and experienced CMV infections. CMVs are normally present in body liquids such as blood, lymph, saliva, urine, feces, milk, etc. CMV infections may cause abortion, stillbirth, postnatal death from hemorrhage, anemia, severe hepatic or CNS damage. Particularly dangerous are CMV infections afflicting AIDS patients, where CMV may cause pulmonary, gastrointestinal or renal complications. There is no specific therapy for CMVs. Unlike HSV, CMV is resistant to acyclovir, and to other known antiviral drugs.

Thus, it would be extremely advantageous to have available a drug which would effectively inhibit CMV infections.

Recently, a series of highly effective anti-tumor and anti-viral drugs were identified. These drugs include: substituted and unsubstituted 6-amino-1,2-benzopyrones which are the subject of copending U.S. patent application Ser. No. 07/845,342 filed on Mar. 4, 1992, entitled "6-Amino-1,2-Benzopyrones Useful for Treatment of Viral Diseases;" 5-iodo-6-amino-1,2-benzopyrones and 5-iodo-6-nitroso-1,2-benzopyrones which are the subject of U.S. Pat. No. 5,484,951 issued on Jan. 16, 1996 entitled "Novel 5-Iodo-6-Amino-1,2-Benzopyrones and Their Metabolites Useful as Cytostatic and Antiviral Agents" and Ser. No. 08/021,989 filed on Feb. 24, 1993 entitled "Novel 5-Iodo-6-Amino-1,2-Benzopyrones and Their Metabolites Useful as Cytostatic Agents;" 3-nitrosobenzamides, 6-nitroso-1,2-benzopyrones and nitroso-1-(2H)-isoquinolinones which are the subject of copending U.S. patent application Ser. Nos. 07/780,809, 07/893,429 and 07/965,541 filed Oct. 22, 1991, Jun. 4, 1992 and Nov. 2, 1992, respectively, and entitled "Adenosine Diphosphoribose Polymerase Binding Nitroso Aromatic Compounds Useful As Retroviral Inactivating Agents, Antiretroviral Agents and Anti-tumor Agents;" various halo-nitro compounds which are the subject of copending U.S. patent application Ser. No. 08/060,409 filed May 12, 1993 entitled "Novel Aromatic Compounds and Their Metabolites Useful as Anti-viral and Anti-tumor Agents" the disclosures of which are incorporated herein by reference.

These drugs are of remarkably low toxicity, yet highly effective inhibitors of tumor and viral replication in cell cultures and in human blood. Their therapeutic spectrum appear to be particularly useful for suppression and inhibition of cancer growth and for treatment of the most dangerous viral infections, such as AIDS and herpetic infections.

The mechanisms of action of the the C-nitroso drugs have been recently elucidated. Recently published experiments have shown that aromatic C-nitroso ligands of poly (ADP-ribose) polymerase preferentially destabilize one of the two zinc fingers of the enzyme coincidental with a loss of enzymatic activity but not DNA binding capacity of the protein (Buki, et al., FEBS Lett. 290:181–185 (1991)). Based on the similarity to results obtained by site-directed mutagenesis (Gradwohl, et al., Proc. Natl. Sci. USA 87:2990–2992 (1990)), it appears that the primary attack of C-nitroso ligands occurred at zinc finger FI (Buki, et al., FEBS Lett. 290:181–185 (1991)). 6-nitroso-1,2 benzopyrone (6-NOBP) and 3-nitrosobenzamide (3-NOBA), two C-nitroso compounds that inactivate ADPRT at one zinc finger site completely suppressed the proliferation of leukemic and other malignant human cells and subsequently produced cell death. Tumoricidal concentrations of the drugs were relatively harmless to normal bone marrow progenitor cells and to superoxide formation by neutrophil granulocytes. The cellular mechanisms elicited by the C-nitroso compounds consists of apoptosis due to DNA degradation by the nuclear calcium/magnesium dependent endonuclease (Rice et al. Proc. Natl. Sci. USA (1992) 89:7703–7707). This endonuclease is maintained in a latent form by poly(ADP-ribosyl)ation, but inactivation of ADPRT by C-nitroso drugs derepresses the DNA-degrading activity. Therefore, the C-nitroso compounds are effective anti-tumor compounds.

Retroviral nucleocapsid (NC) proteins and their respective gag precursors from all strains of known retroviruses contain at least one copy of a zinc-binding polypeptide sequence of the type Cys-X2-Cys-X$_4$-His-X$_4$-Cys (CCHC) (Henderson, et al., Biol. Chem. 256:8400–8406 (1981)), i.e., a zinc finger domain. This CCHC sequence is essential for maintaining viral infectivity, (Gorelick, et al., Proc. Natl. Acad. Sci. USA 85:8420–8424 (1988), Gorelick, et al., J. Virol. 64:3207–3211 (1990)), therefore, it represents an attractive target for viral chemotherapy. The HIV-1 gag proteins function by specifically binding to the HIV-1 RNA, anchoring it to the cell membrane for budding or viral particles (Meric, et al., J. Virol. 63: 1558–1658 (1989) Gorelick, et al., Proc. Natl. Acad. Sci. USA 85:8420–8424 (1988), Aldovini, et al., J. Virol. 64:1920–1926 (1990), Lever, et al., J. Virol. 63:4085–4087 (1989)). Site-directed mutagenesis studies demonstrated that modification of Cys or His residues results in defective viral RNA packaging and noninfectious viral particles are formed (Aldovini, et al., J. Virol. 64:1920–1926 (1990), Lever, et al., J. Virol. 63:4085–4087 (1989)).

Based on the occurrence of (3Cys, 1His) zinc binding sites in both retroviral nucleocapsid and gag-precursor proteins and in poly(ADP-ribose) polymerase it was reasoned that C-nitroso compounds may also have anti-retroviral effects. Recently it was demonstrated that 3-NOBA and 6-NOBP inhibit infection of human immunodeficiency virus HIV-1 in human lymphocytes and also eject zinc from isolated HIV-1 NC zinc fingers and from intact HIV-1 virions. The zinc-ejected HIV-1 virions exhibit complete loss of infectivity in human lymphocytes. Therefore, the C-nitroso compounds are effective anti-viral compounds.

While these C-nitroso compounds have been found to be quite effective in preliminary in vitro tests, they are relatively water insoluble at physiological pH, exhibit limited stability and limited predictability of delivery to the affected cells due to their solubility and stability characteristics. It is thus of interest to identify stable precursor molecules to serve as pro-drugs for the active C-nitroso compounds, especially the aromatic C-nitroso compounds. These pro-drugs would be converted to the active C-nitroso compounds in vivo. Ideally, these pro-drugs would be stable and soluble for convenient use as anti-retroviral and anti-cancer compositions.

Halo nitro compounds are reduced in vivo to active halo nitroso compounds and therefore provide a ready source of in vivo anti-tumor and anti-retroviral C-nitroso compounds.

4-iodo-3-nitrobenzamide (4-I-3-NO$_2$BA) has not been hitherto known or described. Three structural isomers of 4-I-3-NO$_2$BA are known in the literature: 2-iodo-4-nitrobenzamide, 2-iodo-5-nitrobenzamide and 3-iodo-5-nitrobenzamide (Chem Abstracts: 101: 230049f (1983), 24:3367 (1930) and 97:23081n (1982). No medical use was reported for the compounds.

Halo nitro and nitroso estrogen compounds including halo-nitro-estradiol, halo-nitroso-estradiol, halo-nitro-estrone, halo-nitroso-estrone, halo-nitro-estriol, halo-nitroso-estriol, halo-nitro-equilenin, halo-nitroso-equilenin, halo-nitro-equilin and halo-nitroso-equilin, halo-nitro-stilbestrol, halo-nitroso-stilbestrol find use as effective anti-tumor agents for treating breast cancer. The estrogen molecules specifically target the active nitro or nitroso moieties to the cancerous breast cells. As indicated above, these cancerous cells are specifically inactivated.

It is therefore a primary object of this invention to provide stable, soluble, non-toxic, highly effective antineoplastic and antiviral drugs. Halo nitro compounds including halo-nitro-estradiol, halo-nitroso-estradiol, halo-nitro-estrone, halo-nitroso-estrone, halo-nitro-estriol, halo-nitroso-estriol, halo-nitro-equilenin, halo-nitroso-equilenin, halo-nitro-equilin, halo-nitroso-equilin, halo-nitro-stilbestrol, halo-nitroso-stilbestrol, 5-iodo-6-nitro-1,2-benzopyrones, 6-nitro-1,2-benzopyrone, 3-nitrobenzamide, 5-nitro-1(2H)-isoquinoline, 7-nitro-1(2H)-isoquinoline, 8-nitro-1(2H)-isoquinoline, 2-nitrobenzamide, 4-nitrobenzamide and their homologues demonstrate these desired properties.

SUMMARY

One aspect of the current invention concerns novel cytostatic anti-tumorigenic and anti-viral compounds of the formula:

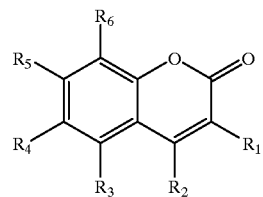

wherein $R_1$, $R_2$, $R_3$, $R_4$, $R_5$ and $R_6$ are, independent of one another, selected from the group consisting of hydrogen, hydroxy, amino, nitroso, nitro, halogen, ($C_1$–C6) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are always hydrogen.

Another aspect of the current invention relates to novel cytostatic and antiviral agents having the formula:

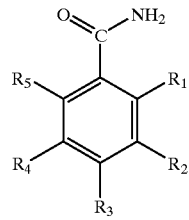

wherein $R_1$, $R_2$, $R_3$, $R_4$ and $R_5$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are always hydrogen.

Another aspect of the current invention relates to novel cytostatic and antiviral agents having the formula:

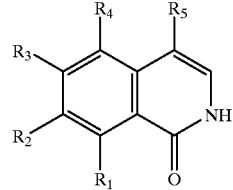

wherein $R_1$, $R_2$, $R_3$, $R_4$ and $R_5$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are always hydrogen.

Still yet another aspect of the current invention concerns a method for inhibiting or suppressing tumorigenic growth or for treatment of viral infections in a mammal comprising administering to a mammal a therapeutically effective amount of a compound of the formula:

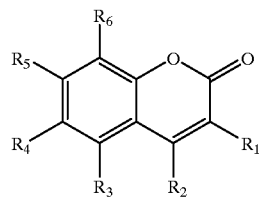

(I)

wherein
$R_1, R_2, R_3, R_4, R_5$ and $R_6$ are, independent of one another, selected from the group consisting of hydrogen, hydroxy, amino, nitroso, nitro, halogen, $(C_1$–$C_6)$ alkyl, $(C_1$–$C6)$ alkoxy, $(C_3$–$C_7)$ cycloalkyl, and phenyl and pharmaceutically acceptable salts thereof, wherein at least three of the six $R_1, R_2, R_3, R_4, R_5$ and $R_6$ substituents are always hydrogen.

Still another aspect of the current invention concerns a method for inhibiting or suppressing tumorigenic growth or for treatment of viral infections in a mammal comprising administering to a mammal a therapeutically effective amount of a compound of the formula:

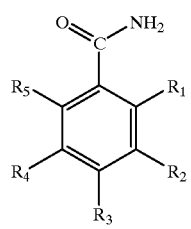

(II)

wherein
$R_1, R_2, R_3, R_4$ and $R_5$ are, independent of one another, selected from the group consisting of hydrogen, hydroxy, amino, nitroso, nitro, halogen, $(C_1$–$C_6)$ alkyl, $(C_1$–$C_6)$ alkoxy, $(C_3$–$C_7)$ cycloalkyl, and phenyl and pharmaceutically acceptable salts thereof, wherein at least two of the five $R_1, R_2, R_3, R_4$ and $R_5$ substituents are always hydrogen.

Still another aspect of the current invention concerns a method for inhibiting or suppressing tumorigenic growth or for treatment of viral infections in a mammal comprising administering to a mammal a therapeutically effective amount of a compound of the formula:

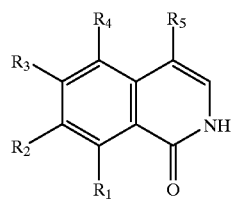

(III)

wherein
$R_1, R_2, R_3, R_4$ and $R_5$ are, independent of one another, selected from the group consisting of hydrogen, hydroxy, amino, nitroso, nitro, halogen, $(C_1$–$C_6)$ alkyl, $(C_1$–$C_6)$ alkoxy, $(C_3$–$C_7)$ cycloalkyl, and phenyl and pharmaceutically acceptable salts thereof, wherein at least two of the five $R_1, R_2, R_3, R_4$ and $R_5$ substituents are always hydrogen.

Still yet another aspect of this invention is the method of preparation of the compound of formula

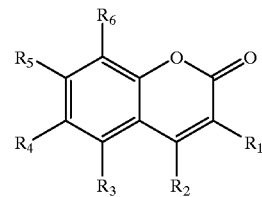

(I)

wherein
$R_1, R_2, R_3, R_4, R_5$ and $R_6$ are, independent of one another, selected from the group consisting of hydrogen, hydroxy, amino, nitroso, nitro, halogen, $(C_1$–$C_6)$ alkyl, $(C_1$–$C6)$ alkoxy, $(C_3$–$C_7)$ cycloalkyl, and phenyl and pharmaceutically acceptable salts thereof, wherein at least three of the six $R_1, R_2, R_3, R_4, R_5$ and $R_6$ substituents are always hydrogen.

Still yet another aspect of this invention is the method of preparation of the compound of formula

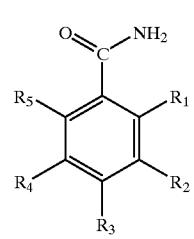

(II)

wherein
$R_1, R_2, R_3, R_4$ and $R_5$ are, independent of one another, selected from the group consisting of hydrogen, hydroxy, amino, nitroso, nitro, halogen, $(C_1$–$C_6)$ alkyl, $(C_1$–$C_6)$ alkoxy, $(C_3$–$C_7)$ cycloalkyl, and phenyl and pharmaceutically acceptable salts thereof, wherein at least two of the five $R_1, R_2, R_3, R_4$ and $R_5$ substituents are always hydrogen.

Still yet another aspect of this invention is the method of preparation of the compound of formula

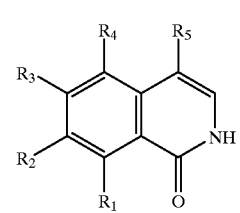

(III)

wherein
$R_1, R_2, R_3, R_4$ and $R_5$ are, independent of one another, selected from the group consisting of hydrogen, hydroxy, amino, nitroso, nitro, halogen, $(C_1$–$C6)$ alkyl, $(C_1$–$C_6)$ alkoxy, $(C_3$–$C_7)$ cycloalkyl, and phenyl and pharmaceutically acceptable salts thereof, wherein at least two of the five $R_1, R_2, R_3, R_4$ and $R_5$ substituents are always hydrogen.

Another aspect of the current invention relates to novel cytostatic and antiviral agents and methods of synthesis thereof having the formula:

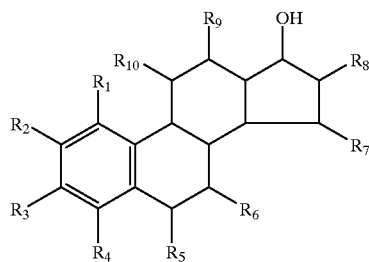

(IV)

wherein
$R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, $(C_1-C_6)$ alkyl, $(C_1-C_6)$ alkoxy, $(C_3-C_7)$ cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are always hydrogen.

Another aspect of the current invention relates to novel cytostatic and antiviral agents and methods of synthesis thereof having the formula:

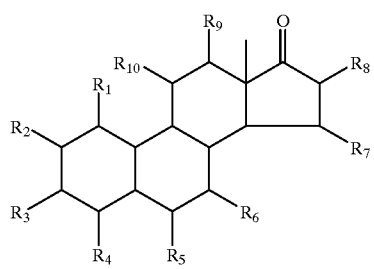

(V)

wherein
$R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, $(C_1-C_6)$ alkyl, $(C_1-C_6)$ alkoxy, $(C_3-C_7)$ cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are always hydrogen.

Another aspect of the current invention relates to novel cytostatic and antiviral agents and methods of synthesis thereof having the formula:

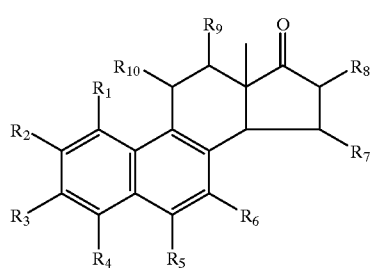

(VI)

wherein
$R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, $(C_1-C_6)$ alkyl, $(C_1-C_6)$ alkoxy, $(C_3-C_7)$ cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are always hydrogen.

Another aspect of the current invention relates to novel cytostatic and antiviral agents and methods of synthesis thereof having the formula:

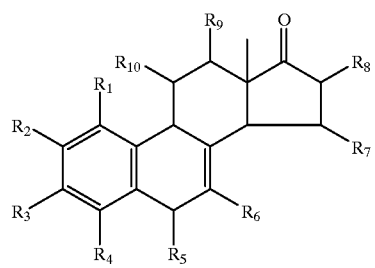

(VII)

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, $(C_1-C_6)$ alkyl, $(C_1-C_6)$ alkoxy, $(C_3-C_7)$ cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are always hydrogen.

Another aspect of the current invention relates to novel cytostatic and antiviral agents and methods of synthesis thereof having the formula:

(VIII)

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, $(C_1-C_6)$ alkyl, $(C_1-C_6)$ alkoxy, $(C_3-C_7)$ cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are always hydrogen.

Another aspect of the current invention relates to novel cytostatic and antiviral agents and methods of synthesis thereof having the formula:

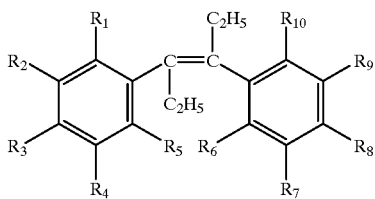

(IX)

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are always hydrogen.

In a preferred mode, the halo and nitro groups of compounds I–IX are attached to adjacent carbon atoms.

DETAILED DESCRIPTION OF THE INVENTION

Definitions

Figure 1:
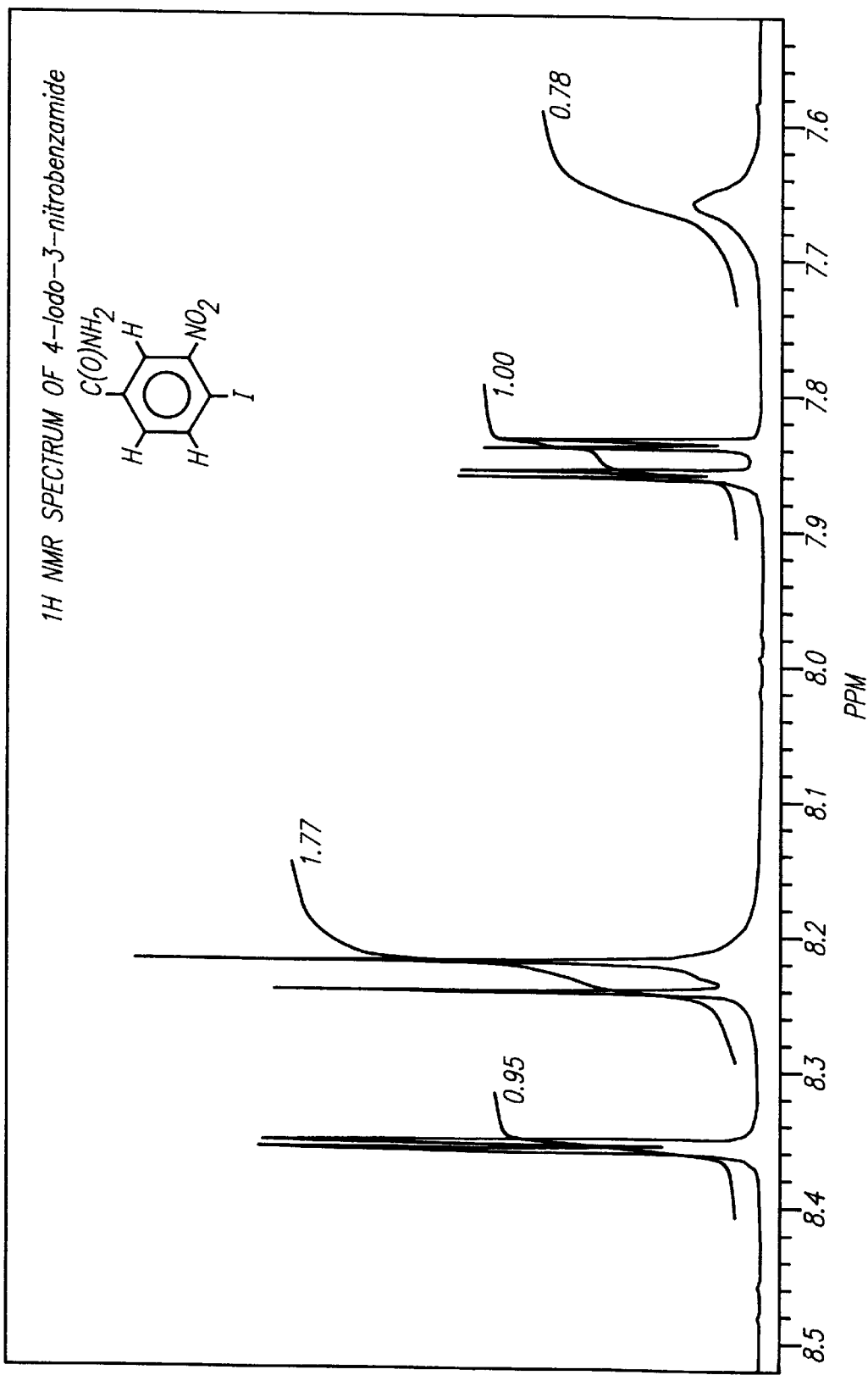
FIG. 1 shows $^1$H NMR spectrum of isolated 4-iodo-3-nitrobenzamide.

As used herein:

"Viral diseases" mean viral infections caused by retrovirus and lentivirus such as HIV-1, HIV-2, animal viruses, neurological sheep viruses, HSV-1, HSV-2, herpes zoster, CMV, Epstein Barr virus and other viruses belonging to the same class.

"Pharmaceutically acceptable acid addition salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"ADPRT" refers to adenosinediphosphoribose transferase also known as poly (ADP-ribose)polymerase, (EC 2.4.99), a specific DNA-binding nuclear protein of eucaryotes that catalyzes the polymerization of ADP-ribose. The enzymatic process is dependent on DNA.

"Alkyl" refers to saturated or unsaturated branched or straight chain hydrocarbon radical. Typical alkyl groups includes methyl, ethyl, propyl, isopropyl, butyl, isobutyl, tertiary butyl, pentyl, hexyl and the like.

"Alkoxy" refers to the radical —O-alkyl. Typical alkoxy radicals are methoxy, ethoxy, propoxy, butoxy and pentoxy and the like.

"Cycloalkyl" refers to a saturated monocyclic hydrocarbon radical containing 3–8 carbon atoms such as cyclopropyl, cyclobutyl, cyclopentyl, cyclohexyl, cycloheptyl and cyclooctyl.

"Substituted phenyl" refers to all possible isomeric phenyl radicals mono or disubstituted with a substituent selected from the group consisting of alkyl, alkoxy, hydroxy or halo.

"Halo" refers to chloro, fluoro, bromo or iodo.

Utility

The halo-nitro and halo-nitroso compounds (I–IX) of this application are potent, specific and non-toxic antineoplastic and antiviral drugs which selectively inhibit growth of tumor cells and virus reproduction. These compounds find use particularly in treating breast cancer. These compounds also find use particularly against viruses such as human immunodeficiency viruses, HIV-1, HIV-2, herpetic viruses, HSV-1, HSV-2, herpes zoster or, Epstein Barr virus (EBV), animal viruses, neurological sheep viruses, and CMV. Consequently, these drugs are useful for prevention and treatment of tumorous and viral diseases. These compounds are particularly effective inhibitors of tumor growth in immunosuppressed patients with AIDS where they affect not only the tumor growth such as Kaposi's sarcoma but also inhibit human immunodeficiency virus, and the development of opportunistic infection due to herpes simplex virus and cytomegalovirus and opportunistic neoplastic growths such as Kaposi sarcoma, nonHodgkin lymphoma and primary lymphoma. In the case of viruses, these compounds are thus particularly useful for treatment of AIDS, herpetic lesions and cytomegalovirus infection. Moreover, these compounds have very low, if any, toxicity.

Antiviral Activity of Nitro-Compounds

The halo-nitro compounds (I–IX) of this application are in vivo precursors of potent anti-viral drugs. (Table 2). 6-Nitro-1,2-benzopyrone, an in vivo pro-drug of 6-nitroso-1,2-benzopyrone-6NOBP inhibited HIV-1 activity in human lymphocytes 52% by reduction to the active nitroso form in vivo. Since the nitro compound is more stable and soluble than the active nitroso compound, which in the solid form is a poorly soluble dimeric species, supplying the nitro pro-drug provides a constant in vivo supply of the active nitroso compound for inhibiting viral growth and reproduction.

Cytostatic Effects of Nitro Compounds

The halo nitro compounds (I–IX) also possess very potent cytostatic anti-tumorigenic activity. Such activity has been studied on cells lines and is described in detail in Example 1.

Figure 3:
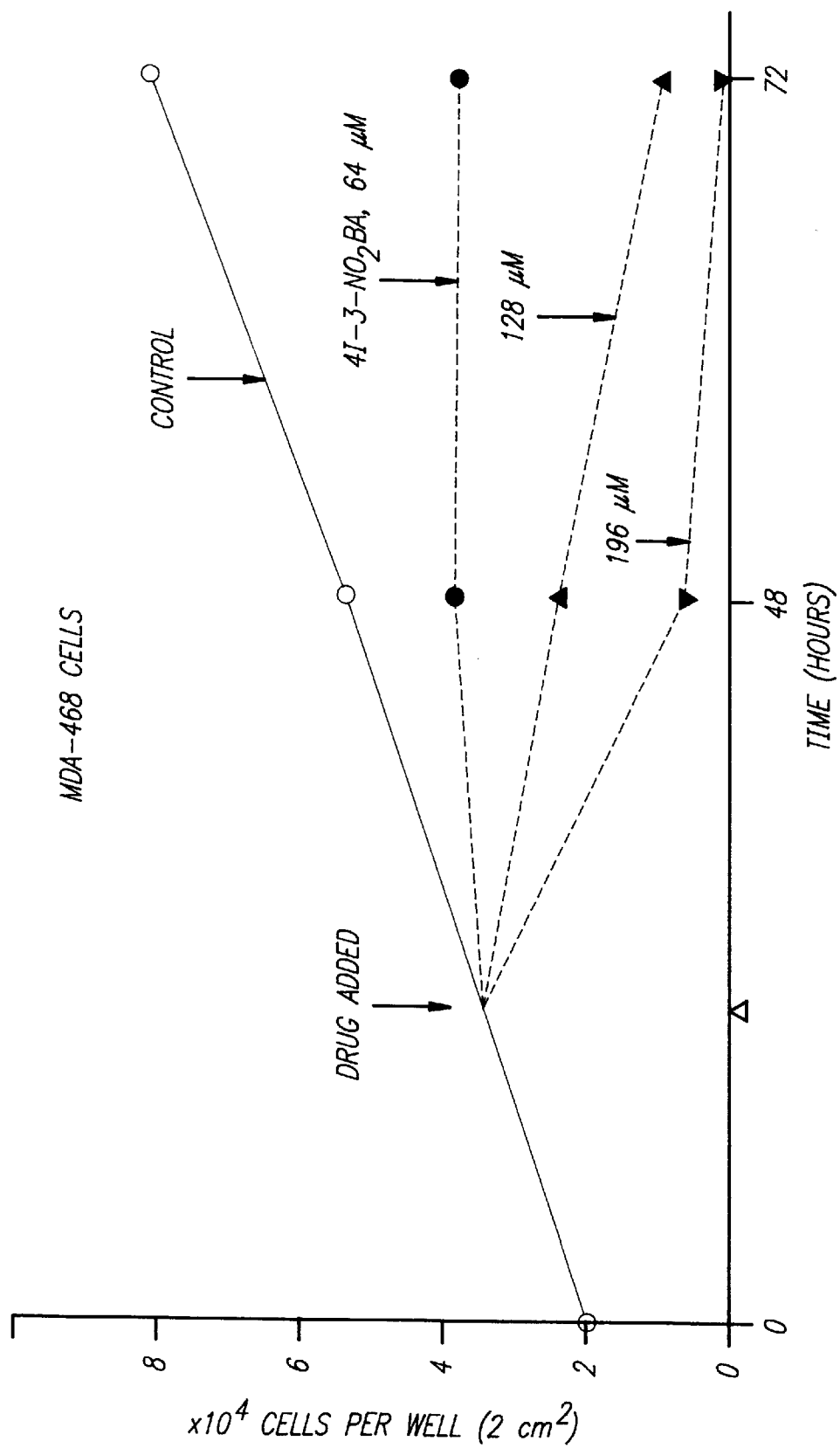
FIG. 3 shows the effect of various concentrations of 4-iodo-3-nitrobenzamide on the growth of MDA-468 cancer cells.

FIG. 3 shows the effect of various concentrations of 4-iodo-3-nitrobenzamide on the growth of MDA-468 cancer cells is demonstrated.

Figure 4:
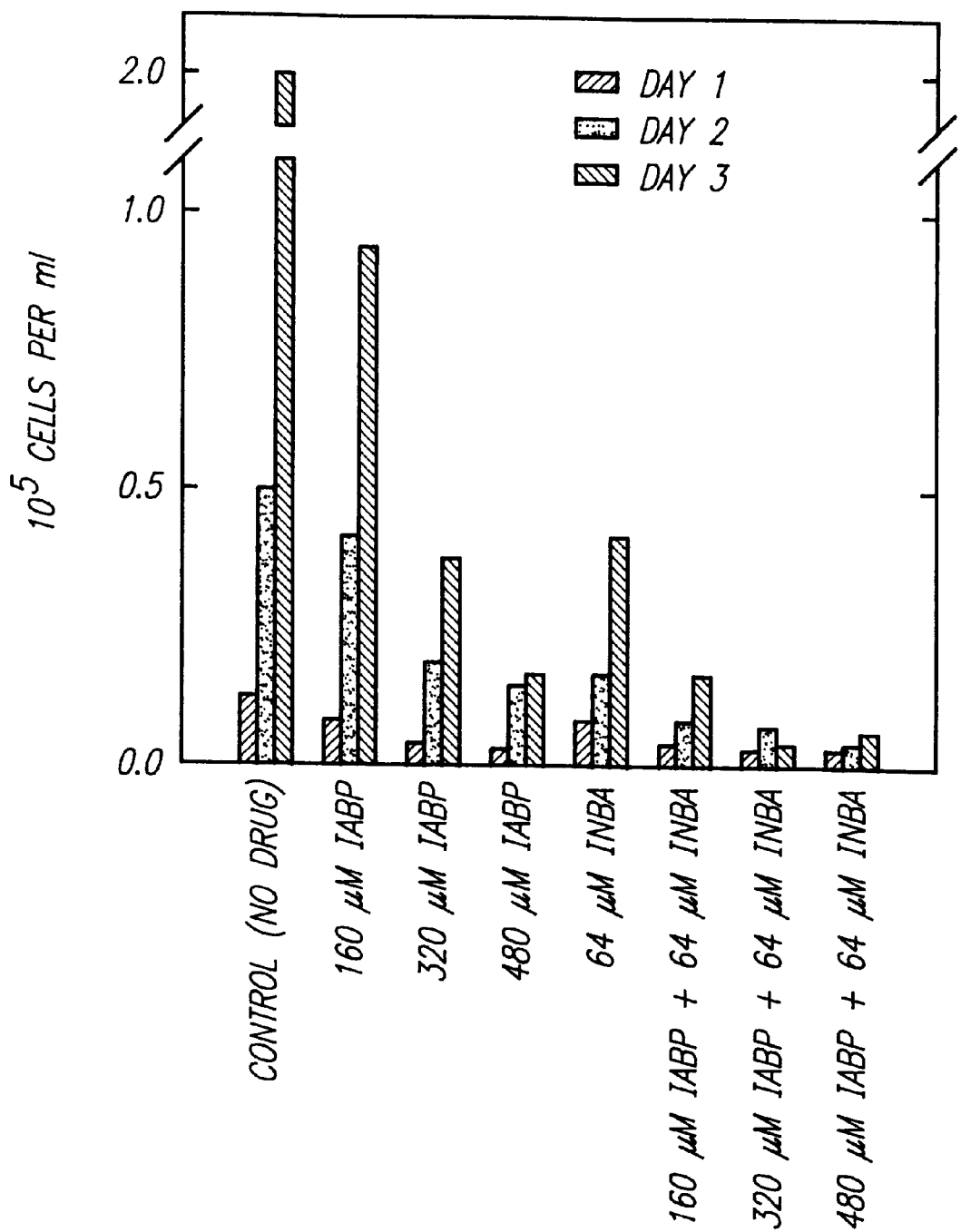
FIG. 4 shows the effect of 5-iodo-6-amino-1,2-benzopyrone (IABP) and 4-iodo-3-nitrobenzamide (INBA) alone and in combination on the growth of L1210 cancer cells.

FIG. 4 shows the effect of 5-iodo-6-amino-1,2-benzopyrone (IABP) and 4-iodo-3-nitrobenzamide (INBA) alone and in combination on the growth of L1210 cancer cells.

In practice, the compounds of this invention, namely substituted or unsubstituted halo nitro compounds of formulae I–IX or any of their pharmaceutically acceptable salts, will be administered in amounts which will be sufficient to inhibit the neoplastic growth or the viral expression or prevent the development of the cancerous growth or viral infection in the host cell and in the pharmaceutical form most suitable for such purposes.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is intravenous, except in those cases where the subject has topical tumors or lesions, where the topical administration may be proper. In other instances, it may be necessary to administer the composition in other parenteral or even oral forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an effective amount of active halo nitro compounds of formula I–IX or the pharmaceutically acceptable salt thereof, and in addition, it may include any conventional pharmaceutical excipients and other medicinal or pharmaceutical drugs or agents, carriers, adjuvants, diluents, etc., as customary in the pharmaceutical sciences.

For solid compositions such excipients include pharmaceutical grades of mannitol, lactose, starch, magnesium stearate, sodium saccharin, talcum, cellulose, glucose, sucrose, magnesium carbonate, and the like may be used. The active halo-nitro and halo-nitroso compounds I–IX as defined above, may be also formulated as suppositories using, for example, polyalkylene glycols, for example, propylene glycol, as the carrier.

Liquid, particularly injectable compositions can, for example, be prepared by dissolving, dispersing, etc. an active compound I–IX in a pharmaceutical solution such as, for example, water, saline, aqueous dextrose, glycerol, ethanol, and the like, to thereby form the injectable solution or suspension.

If desired, the pharmaceutical composition to be administered may also contain minor amounts of nontoxic auxiliary substances such as wetting or emulsifying agents, pH buffering agents, and the other substances such as for example, sodium acetate, triethanolamine oleate, etc.

If desired, the pharmaceutical composition to be administered may contain liposomal formulations comprising a phospholipid, a negatively charged phospholipid and a compound selected from cholesterol, a fatty acid ester of cholesterol or an unsaturated fatty acid. The halo nitro compounds may be encapsulated or partitioned in a bilayer of liposomes of the liposomal formulation according to U.S. patent application Ser. No. 08/020,035 entitled "Liposomal Formulations and Methods of Making and Using Same" filed on Feb. 19, 1993 which is incorporated herein by reference.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

A more recently devised approach for parenteral administration employs the implantation of a slow-release or sustained-released systems, which assures that a constant level of dosage is maintained, according to U.S. Pat. No. 3,710,795, which is incorporated herein by reference.

Any of the above pharmaceutical compositions may contain 0.1–99%, preferably 1–70% of the active halo nitro ingredients.

Actual methods of preparing such dosage forms are known, or will be apparent to those skilled in this art, and are in detail described in *Remington's Pharmaceutical Sciences,* Mack Publishing Company, Easton, Pa., 17th Edition, 1985. The composition or formulation to be administered will, in any event, contain such quantity of the active compound(s) which will assure that a therapeutically effective amount will be delivered to a patient. The therapeutically effective amount means an amount effective to prevent development of or to alleviate the existing symptoms of the subject being treated.

The amount of active compound administered will, of course, be dependent on the subject being treated, on the subject's weight, the severity of the affliction, the manner of administration and the judgment of the prescribing physician. However, an effective dosage is in the range of 0.001 to 5000 mg/kg/day, preferably 0.01 to 1000 mg/kg/day, more preferably 0.1 to 100 mg/kg/day. Generally, the upper limit for the drug dose determination is its efficacy balanced with its possible toxicity. However, since such toxicity has not been observed in animal (rodent) experiments for the compounds of this invention, the administered dose may be as high as needed to achieve desirable therapeutical effect.

Various substituents of the halo nitro compounds as shown in formulae, are likely to modify lipid solubility rate of cellular penetration, thus clinical dosage schedules the above biochemical mechanism is not likely to be altered on a molecular level by substituents.

The chemotherapy may be repeated intermittently while tumors or HIV infections are or even when they are not detectable.

Moreover, due to its apparent nontoxicity, the therapy may be provided alone or in combination with other antiviral or other drugs, such as for example AZT, anti–inflammatories antibiotics, corticosteroids, vitamins and other such drugs. There are no contraindications to use halo nitro compounds with even such toxic drugs as AZT since halo nitro compounds are nontoxic and their modes of action are quite different. Possible synergism between halo nitro compounds and other drugs is expected and predictable.

Halo nitro compounds are equally useful for treatment of herpetic lesions caused by both HSV-1 and HSV-2. The drug would be preferably administered by i.v. infusion or other parenteral or systemic mode of administration. In case of sores, the drug could be also administered topically. Infection caused by CMV would be treated preferably in the same fashion as that suggested for AIDS treatment.

The following preparations and examples serve to illustrate the invention. They should not be construed as narrowing it, or limiting its scope.

I. Preparation of 4-Iodo-3-nitrobenzamide

In a 100-mL flask equipped with a magnetic stirrer, thermometer and ice bath, a stirred solution of 4-Iodo-3-nitrobenzoic acid (1025 mg (3.50 mMoles), Chemica Alta Ltd., Edmonton, Alberta, Canada) in N,N-dimethylformamide (10 mL) is cooled to 10° C., and then thionyl chloride (0.76 mL, 10.5 mMoles) is added to it. There is no exothermicity, the ice bath is removed, and the solution is allowed to warm to ambient temperature, and stirring is continued for a total of 1 hour. Then the solution is poured into chilled, concentrated ammonium hydroxide (20 mL), resulting in a dark yellow mixture, which is stirred for 5 minutes. Then chilled deionized water (50 mL) is added, causing precipitation of the light yellow product. After allowing the precipitation mixture to stand chilled on ice for 10 minutes, the precipitate is collected on a suction filter, rinsed with cold water, and then dried by vacuum pumping. The resultant crude product (500.4 mg) is then re-crystallized by dissolving it in acetonitrile (7.0 mL) heated to about 65° C., followed by cooling and allowing the solution to stand in the refrigerator overnight. The yellow crystals are collected, rinsed with chilled solvent and dried by vacuum pumping, to give 415.2 mg (40.5% yield) of 4-Iodo-3-nitrobenzamide, m.p. 152–155° C.

$^1$H NMR spectrum, FIG. 1, in DMSO-$d_6$ ($\delta$ (ppm) values relative to TMS): broad singlet (7.67) due to one nonequivalent proton of the amido $NH_2$ group; doublet of doublets (7.84, 7.85 and 7.86, 7.87) due to H-5 split by H-6 and finely split by H-2; doublet (8.22, 8.24) due to H-6 split by H-5; broad singlet centered near 8.22, overlapping the signal of H-6, due to the second nonequivalent proton of the amido $NH_2$ group; doublet (8.35, 8.36) due to H-2 finely split by H-5. At higher NMR field (not shown in FIG. 1) signals due to adventitious water (2.5 ppm), deuterated-DMSO impurity protons (3.3 ppm) and crystallization solvent acetonitrile (singlet at 2.07 ppm) are observed. Integration of the acetonitrile signal indicates approximately one molecule of acetonitrile per 3 molecules of 4-iodo-3-nitrobenzamide.

UV absorption spectrum in absolute ethanol, λ max (ε): 308 nm ($1.59 \times 10^3$), 242 nm ($1.31 \times 10^4$), 208 nm ($1.45 \times 10^4$).

Figure 2:
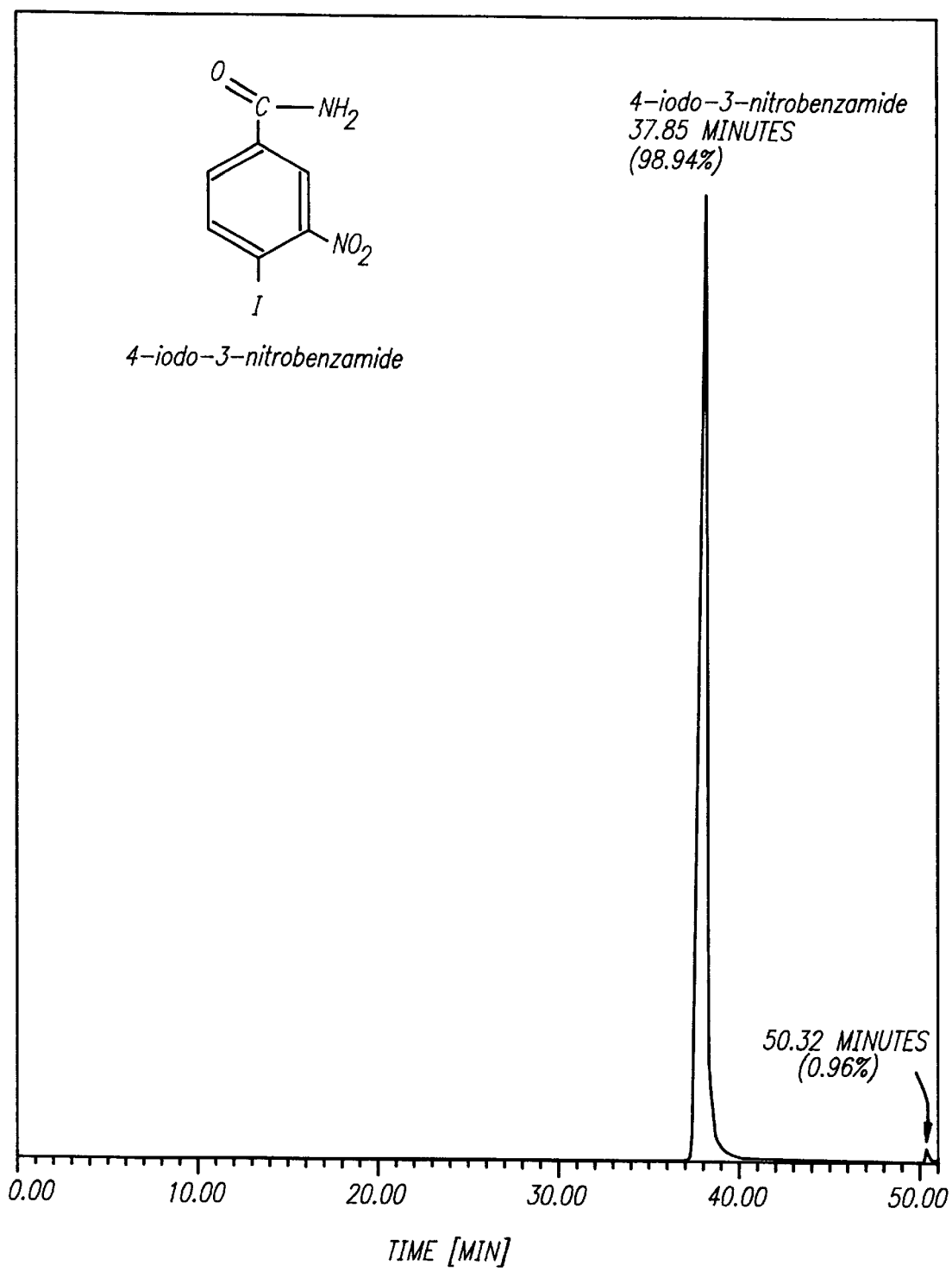
FIG. 2 shows the HPLC chromatogram of purified 4-iodo-3-nitrobenzamide.

High Performance Liquid Chromotography (HPLC) HPLC is carried out on a reversed-phase ultrasphere ODS column (FIG. 2). A sample of 4-iodo-3-nitrobenzamide in ethanol is injected and elution is by a ternary solvent gradient system (aqueous phosphate buffer (pH 6.8)/30% aqueous (buffer) methanol/50% aqueous acetonitrile). Flow rate is 1.2 ml/min and UV detection is at 260 nm.

Elemental analysis (Schwarzkopf Microanalytical Laboratory): Calculated for $C_7H_5IN_2O_3$: C, 28.79%; H, 1.73; I, 43.46; N, 9.59. Found: C, 29.63; H, 1.72; I, .41.47; N, 9.99. Deviations from calculated are believed to be due to the presence of acetonitrile (crystallization solvent) as detected in the NMR spectrum.

TABLE 1

I 50 and LD 100 values for Nitroso- and Nitro-compounds in mammary cancer cells (monolayer cultures) (A) and in L1210 murine leukemia cells (suspension culture) (B)

| | [nanomoles/cm × $10^4$ cells] | | | | | |
|---|---|---|---|---|---|---|
| (A) | MDA 468 | | MCF-7 | | BT 474 | |
| Cell line: | I 50 | LD100 | I 50 | LD100 | I 50 | LD100 |
| 3-NOBA 4-I-3-$NO_2$ BA | 85 | 195 | 100 | 250 | 90 | 200 |
| 4-I-3-$NO_2$ benzoic acid | 180 | n.d. | 145 | n.d. | 160 | n.d. |
| 6-$NO_2$BP | 260 | n.d. | 250 | n.d. | 260 | n.d. |

Seeding was at $2 \times 10^4$ or $0.8 \times 10^4$ cells/cm$^2$, drugs were added 6–18 hours after seeding, and drug exposure time was 24–48 hours.

| | [nanomoles/$10^5$ cells] | |
|---|---|---|
| (B) L1210 cells: | I 50 | LD100 |
| 3-NOBA | 7.5 | 15 |
| 4-I-3-$NO_2$ BA | 16 | 32 |
| 4-I-3-$NO_2$ benzoic acid | 16 | 32 |
| 6-$NO_2$BP | 35 | 80 |

Cells were seeded at $5 \times 10^4$ to $2 \times 10^5$/ml; drugs were added at the time of seeding; drug exposure was for 18 hours.

A time course experiment of the effect of increasing concentrations of 4-iodo-3-nitrobenzamide the growth of MDA-468 cancer cells is shown in FIG. 3.

The synergistic effect of 4-iodo-3-nitrobenzamide and 5-iodo-6-amino-1,2-benzopyrone is shown in FIG. 4.

TABLE 2

HIV-1 Activity in Human Lymphocyte of N-Substituted ADPRT Ligands Calculated Infectious Titer of Virus After Treatment

| Treatment | Dose (μM) | $TCID_{50}$ | Decrease | Inhibition |
|---|---|---|---|---|
| No Drug | No Drug | 177,828 | — | — |
| $NH_2$BP | 5000 | 31,623 | 0.75 | 82.22 |
| I-$NH_2$BP | 500 | 45,709 | 0.59 | 74.30 |
| $NO_2$BP | 500 | 85,114 | 0.32 | 52.14 |
| NOBP | 100 | 102 | 3.24 | 99.94 |
| NOBA | 100 | 11 | 4.20 | >99.99 |

6-Nitro-1,2-benzopyrone, an in vivo pro-drug of 6-nitroso-1,2-benzopyrone, inhibited HIV-1 activity in human lymphocytes 52% by reduction to the active nitroso form in vivo. Since the nitro compound is more stable and soluble than the active nitroso compound, which in the solid form is a poorly soluble dimeric species, supplying the nitro pro-drug provides a constant in vivo supply of the active nitroso compound for inhibiting viral growth and reproduction.

II. Synthesis of Halo-nitrosubstituted Estrones

The method of total estrone synthesis of Bachman et al. (J. Amer. Chem. Soc. 64: 974 (1942)) is used for the synthesis of halo-nitro substituted. The starting material and products are compounds of the following formulae:

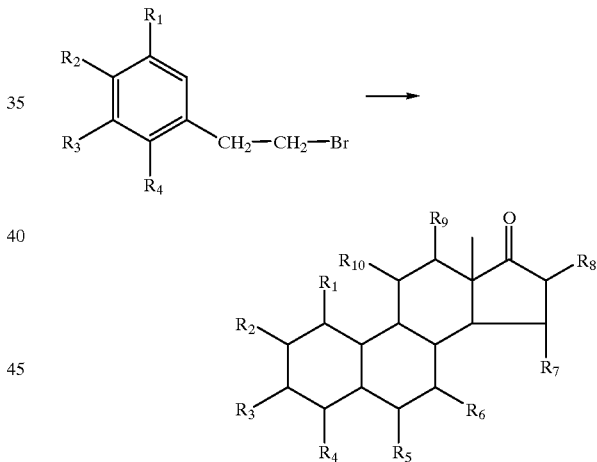

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are always hydrogen.

III. Synthesis of Halo-nitrosubstituted Equilenins

The method of Bachman et al. (J. Amer. Chem Soc. 61: 974 (1939) is used for the synthesis of halo-nitro substituted equilenins. The starting material and products are compounds of the following formulae:

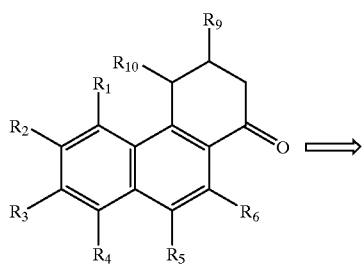

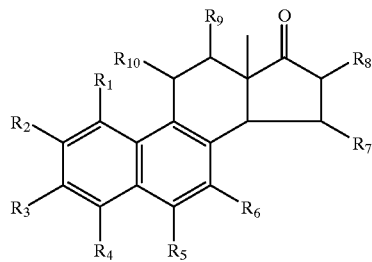

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the nine $R_1$, $R_2$, $R_3$, $R_4$, $R_5$, $R_6$, $R_7$, $R_8$ and $R_9$ substituents are always hydrogen.

Further Examples

In a similar manner as Examples II and III, compounds of formulae IV–IX are synthesized. In a preferred mode, compounds are synthesized with the halo adjacent to the nitro or nitroso group.

The foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

We claim:

1. A method for treating cancer sensitive to treatment, said method comprising the step of administering to a subject, a therapeutically effective amount of a compound selected from the group consisting of:

a compound having the structural formula:

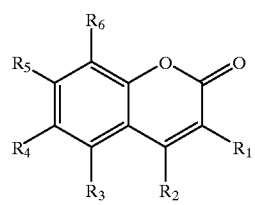

wherein $R_1$, $R_2$, $R_3$, $R_4$, $R_5$ and $R_6$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are always hydrogen and at least one of the six $R_1$, $R_2$, $R_3$, $R_4$, $R_5$ and $R_6$ substituents are always nitro;

a compound having the structural formula:

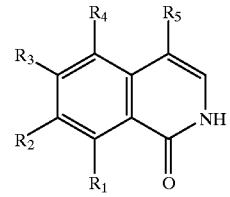

wherein $R_1$, $R_2$, $R_3$, $R_4$ and $R_5$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are always hydrogen and at least one of the five $R_1$, $R_2$, $R_3$, $R_4$ and $R_5$ substituents are always nitro;

a compound having the structural formula:

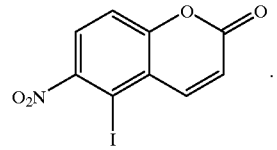

wherein $R_1$, $R_2$, $R_3$, $R_4$ and $R_5$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are always hydrogen and at least one of the five $R_1$, $R_2$, $R_3$, $R_4$ and $R_5$ substituents are always nitro; and a compound having the structural formula:

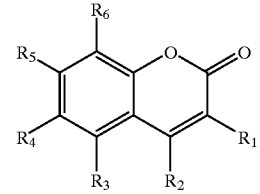

2. The method of claim 1, wherein the compound has the structural formula:

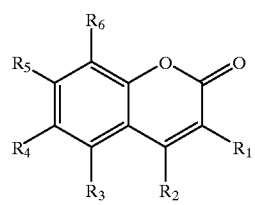

wherein $R_1$, $R_2$, $R_3$, $R_4$, $R_5$ and $R_6$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are always hydrogen and at least one of the six $R_1$, $R_2$, $R_3$, $R_4$, $R_5$ and $R_6$ substituents are always nitro.

3. The method of claim 2, wherein $R_4$ is nitro.

4. The method of claim 2, wherein the halogen is iodine.

5. The method of claim 2, wherein the compound has the structural formula:

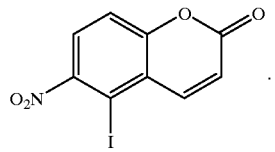

6. The method of claim 2, wherein the compound has the structural formula:

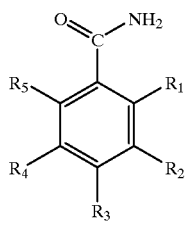

wherein $R_1$, $R_2$, $R_3$, $R_4$ and $R_5$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are always hydrogen and at least one of the five $R_1$, $R_2$, $R_3$, $R_4$ and $R_5$ substituents are always nitro.

7. The method of claim 6, wherein $R_1$, $R_4$ and $R_5$ are each hydrogen; $R_2$ is nitro; and $R_3$ is iodine.

8. The method of claim 2, wherein the compound has the structural formula:

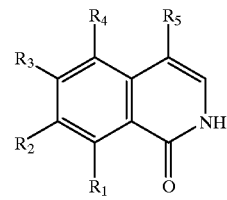

wherein $R_1$, $R_2$, $R_3$, $R_4$ and $R_5$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are always hydrogen and at least one of the five $R_1$, $R_2$, $R_3$, $R_4$ and $R_5$ substituents are always nitro.

9. The method of claim 8, wherein $R_2$ is nitro.

10. The method of claim 8, wherein the halogen is iodine.

11. The method of claim 8, wherein $R_2$ is nitro; $R_1$ is iodine; and $R_3$, $R_4$ and $R_5$ are each hydrogen.

* * * * *

UNITED STATES PATENT AND TRADEMARK OFFICE
CERTIFICATE OF CORRECTION

| | |
|---|---|
| PATENT NO. | : 6,004,978 |
| APPLICATION NO. | : 08/473044 |
| DATED | : December 21, 1999 |
| INVENTOR(S) | : Ernest Kun et al. |

It is certified that error appears in the above-identified patent and that said Letters Patent is hereby corrected as shown below:

In the claims at column 19, line 19, please change:

"claim 2" to --claim 1--

Signed and Sealed this

Eighth Day of December, 2009

David J. Kappos
*Director of the United States Patent and Trademark Office*